(12) United States Patent
Han et al.

(10) Patent No.: US 9,334,502 B2
(45) Date of Patent: May 10, 2016

(54) USE OF HUMAN NLK GENE AND ASSOCIATED DRUGS THEREOF

(75) Inventors: Haixiong Han, Shanghai (CN); Xiangying Zhu, Shanghai (CN); Qin Sun, Shanghai (CN); Xuefeng Gu, Shanghai (CN); Shenghua Xie, Shanghai (CN); Yang Li, Shanghai (CN); Yangsheng Jin, Shanghai (CN); Honghua Qu, Shanghai (CN); Yueqiong Cao, Shanghai (CN)

(73) Assignee: SHANGHAI GENECHEM CO., LTD, Pudong District, Shanghai (CN)

( * ) Notice: Subject to any disclaimer, the term of this patent is extended or adjusted under 35 U.S.C. 154(b) by 0 days.

(21) Appl. No.: 14/367,926

(22) PCT Filed: Jan. 18, 2012

(86) PCT No.: PCT/CN2012/070537
§ 371 (c)(1),
(2), (4) Date: Jun. 22, 2014

(87) PCT Pub. No.: WO2013/091293
PCT Pub. Date: Jun. 27, 2013

(65) Prior Publication Data
US 2015/0005370 A1    Jan. 1, 2015

(30) Foreign Application Priority Data
Dec. 23, 2011   (CN) .......................... 2011 1 0440594

(51) Int. Cl.
*C12N 15/113* (2010.01)

(52) U.S. Cl.
CPC ........ *C12N 15/1137* (2013.01); *C12N 2310/11* (2013.01); *C12N 2310/12* (2013.01);

(Continued)

(58) Field of Classification Search
USPC ............................................ 514/44; 536/24.5
See application file for complete search history.

(56) References Cited

U.S. PATENT DOCUMENTS

2013/0065945 A1*   3/2013   Nam .................... C12Q 1/6886
                                                        514/44 A

FOREIGN PATENT DOCUMENTS

| CN | 101437822 A | 5/2009 |
|---|---|---|
| CN | 101489547 A | 7/2009 |

(Continued)

OTHER PUBLICATIONS

Emami et al., Prostate (2009) vol. 69:1481-1492).*

(Continued)

*Primary Examiner* — Terra C Gibbs
(74) *Attorney, Agent, or Firm* — Global IP Services; Tianhua Gu

(57) ABSTRACT

The present invention discloses the use of a human NLK gene and associated drugs thereof. The present invention discloses the use of the NLK gene for tumor treatment, tumor diagnosis and drug preparation. The present invention further constructs an isolated molecule that attenuates expression of the NLK gene of tumor cells, cells comprising the isolated molecule and a NLK interference lentivirus, and discloses the use thereof as well. The isolated molecule or the NLK interference lentivirus that attenuates expression of the NLK gene provided in the present invention can specifically attenuate expression of the human NLK gene, especially the lentivirus, can effectively infect target cells, efficiently inhibit the expression of the NLK gene in target cells, and inhibit the growth of tumor cells, thus has great significance in tumor treatment.

25 Claims, 4 Drawing Sheets

(52) U.S. Cl.
CPC ....... *C12N2310/14* (2013.01); *C12N 2310/531* (2013.01); *C12N 2799/027* (2013.01); *C12Y 207/11* (2013.01)

(56) References Cited

FOREIGN PATENT DOCUMENTS

WO   WO 2008026075 A2   3/2008
WO   WO 2011118994 A2   9/2011

OTHER PUBLICATIONS

Jung et al. (Journal of Cellular Biochemistry, 2010 vol. 110:687-696).*

Dong, Suwei. NLK-shRNA inhibits tumor cell growth in H1299 lung adenocarcinoma cell line. Chinese Master's Theses Full-text Database Medicine and Health Sciences, Sep. 2011 (Sep. 15, 2011), year 2011, No. 9, EOn-64, ISSN 1674-0246, see the abstract, pp. 9-13, 22-33, figure 3 of p. 22.

Choi, Kwang-Wook et al. Rotation of photoreceptor clusters in the developing drosophila eye requires the nemo gene. Cell, Jul. 15, 1994 (15.07.1994), vol. 78, No. 1, pp. 125-136, ISSN 0092-8674, see p. 129, right column to p. 132, right column, figure 8.

Liu, Hongqiang et al. Development in neuroleukin research. Chinese New Drugs Journal, Oct. 30, 2000, vol. 9, No. 10, pp. 673-676, ISSN 1003-3734, see the whole document, Only Abstract considered.

* cited by examiner

SEQUENCE LISTING

```
<160> NUMBER OF SEQ ID NOS: 44

<210> SEQ ID NO 1
<211> LENGTH: 21
<212> TYPE: DNA
<213> ORGANISM: Homo sapiens
```

```
<400> SEQUENCE: 1
tacagttaag gcgcaccatc a                                              21

<210> SEQ ID NO 2
<211> LENGTH: 21
<212> TYPE: DNA
<213> ORGANISM: Homo sapiens

<400> SEQUENCE: 2
caccatcatc agcactcgca t                                              21

<210> SEQ ID NO 3
<211> LENGTH: 21
<212> TYPE: DNA
<213> ORGANISM: Homo sapiens

<400> SEQUENCE: 3
cagctggata ttgagccgga t                                              21

<210> SEQ ID NO 4
<211> LENGTH: 21
<212> TYPE: DNA
<213> ORGANISM: Homo sapiens

<400> SEQUENCE: 4
cggatagacc tattggatat g                                              21

<210> SEQ ID NO 5
<211> LENGTH: 21
<212> TYPE: DNA
<213> ORGANISM: Homo sapiens

<400> SEQUENCE: 5
gacctattgg atatggagcc t                                              21

<210> SEQ ID NO 6
<211> LENGTH: 21
<212> TYPE: DNA
<213> ORGANISM: Homo sapiens

<400> SEQUENCE: 6
ttggtgttgt ctggtcagta a                                              21

<210> SEQ ID NO 7
<211> LENGTH: 21
<212> TYPE: DNA
<213> ORGANISM: Homo sapiens

<400> SEQUENCE: 7
tggtgttgtc tggtcagtaa c                                              21

<210> SEQ ID NO 8
<211> LENGTH: 21
<212> TYPE: DNA
<213> ORGANISM: Homo sapiens

<400> SEQUENCE: 8
aagggtcttc cgggaattga a                                              21

<210> SEQ ID NO 9
<211> LENGTH: 21
<212> TYPE: DNA
<213> ORGANISM: Homo sapiens
```

```
<400> SEQUENCE: 9
cgggaattga agatgttgtg t                                              21

<210> SEQ ID NO 10
<211> LENGTH: 21
<212> TYPE: DNA
<213> ORGANISM: Homo sapiens

<400> SEQUENCE: 10
aagcatgata atgtactctc t                                              21

<210> SEQ ID NO 11
<211> LENGTH: 21
<212> TYPE: DNA
<213> ORGANISM: Homo sapiens

<400> SEQUENCE: 11
aacctccaca cattgactat t                                              21

<210> SEQ ID NO 12
<211> LENGTH: 21
<212> TYPE: DNA
<213> ORGANISM: Homo sapiens

<400> SEQUENCE: 12
cacagaattg atgcagagtg a                                              21

<210> SEQ ID NO 13
<211> LENGTH: 21
<212> TYPE: DNA
<213> ORGANISM: Homo sapiens

<400> SEQUENCE: 13
aaccactcag ctcagatcat g                                              21

<210> SEQ ID NO 14
<211> LENGTH: 21
<212> TYPE: DNA
<213> ORGANISM: Homo sapiens

<400> SEQUENCE: 14
gctcagatca tgtcaaagtt t                                              21

<210> SEQ ID NO 15
<211> LENGTH: 21
<212> TYPE: DNA
<213> ORGANISM: Homo sapiens

<400> SEQUENCE: 15
tatctccatt cagctggcat t                                              21

<210> SEQ ID NO 16
<211> LENGTH: 21
<212> TYPE: DNA
<213> ORGANISM: Homo sapiens

<400> SEQUENCE: 16
gcaactgtgt tctaaagatt t                                              21

<210> SEQ ID NO 17
<211> LENGTH: 21
<212> TYPE: DNA
```

```
<213> ORGANISM: Homo sapiens

<400> SEQUENCE: 17
aactgtgttc taaagatttg t                                              21

<210> SEQ ID NO 18
<211> LENGTH: 21
<212> TYPE: DNA
<213> ORGANISM: Homo sapiens

<400> SEQUENCE: 18
caggaagttg ttactcagta t                                              21

<210> SEQ ID NO 19
<211> LENGTH: 21
<212> TYPE: DNA
<213> ORGANISM: Homo sapiens

<400> SEQUENCE: 19
aggaagttgt tactcagtat t                                              21

<210> SEQ ID NO 20
<211> LENGTH: 19
<212> TYPE: DNA
<213> ORGANISM: Homo sapiens

<400> SEQUENCE: 20
gcagccgtca ttacagcaa                                                 19

<210> SEQ ID NO 21
<211> LENGTH: 21
<212> TYPE: DNA
<213> ORGANISM: Homo sapiens

<400> SEQUENCE: 21
tgcagaacta ctaggacgaa g                                              21

<210> SEQ ID NO 22
<211> LENGTH: 21
<212> TYPE: DNA
<213> ORGANISM: Homo sapiens

<400> SEQUENCE: 22
agaactacta ggacgaagaa t                                              21

<210> SEQ ID NO 23
<211> LENGTH: 21
<212> TYPE: DNA
<213> ORGANISM: Homo sapiens

<400> SEQUENCE: 23
gaactactag gacgaagaat a                                              21

<210> SEQ ID NO 24
<211> LENGTH: 21
<212> TYPE: DNA
<213> ORGANISM: Homo sapiens

<400> SEQUENCE: 24
aactactagg acgaagaata t                                              21

<210> SEQ ID NO 25
<211> LENGTH: 21
```

```
<212> TYPE: DNA
<213> ORGANISM: Homo sapiens

<400> SEQUENCE: 25
cacaccatca ctggaagcaa t                                              21

<210> SEQ ID NO 26
<211> LENGTH: 21
<212> TYPE: DNA
<213> ORGANISM: Homo sapiens

<400> SEQUENCE: 26
tgaaggcgct aaggcacata t                                              21

<210> SEQ ID NO 27
<211> LENGTH: 21
<212> TYPE: DNA
<213> ORGANISM: Homo sapiens

<400> SEQUENCE: 27
gaaggcgcta aggcacatat a                                              21

<210> SEQ ID NO 28
<211> LENGTH: 21
<212> TYPE: DNA
<213> ORGANISM: Homo sapiens

<400> SEQUENCE: 28
aacagccatc tcttcctgta c                                              21

<210> SEQ ID NO 29
<211> LENGTH: 21
<212> TYPE: DNA
<213> ORGANISM: Homo sapiens

<400> SEQUENCE: 29
caggctacac atgaagctgt t                                              21

<210> SEQ ID NO 30
<211> LENGTH: 21
<212> TYPE: DNA
<213> ORGANISM: Homo sapiens

<400> SEQUENCE: 30
aagctgttca tctcctttgc a                                              21

<210> SEQ ID NO 31
<211> LENGTH: 21
<212> TYPE: DNA
<213> ORGANISM: Homo sapiens

<400> SEQUENCE: 31
ctttgcagga tgttggtctt t                                              21

<210> SEQ ID NO 32
<211> LENGTH: 21
<212> TYPE: DNA
<213> ORGANISM: Homo sapiens

<400> SEQUENCE: 32
tgcaggatgt tggtctttga t                                              21

<210> SEQ ID NO 33
```

```
<211> LENGTH: 21
<212> TYPE: DNA
<213> ORGANISM: Homo sapiens

<400> SEQUENCE: 33
gactttgagc ctgtcaccaa t                                              21

<210> SEQ ID NO 34
<211> LENGTH: 21
<212> TYPE: DNA
<213> ORGANISM: Homo sapiens

<400> SEQUENCE: 34
gagcctgtca ccaatcccaa a                                              21

<210> SEQ ID NO 35
<211> LENGTH: 21
<212> TYPE: DNA
<213> ORGANISM: Homo sapiens

<400> SEQUENCE: 35
aagagcttta ttagttccac t                                              21

<210> SEQ ID NO 36
<211> LENGTH: 21
<212> TYPE: DNA
<213> ORGANISM: Homo sapiens

<400> SEQUENCE: 36
gagctttatt agttccactg t                                              21

<210> SEQ ID NO 37
<211> LENGTH: 21
<212> TYPE: DNA
<213> ORGANISM: Homo sapiens

<400> SEQUENCE: 37
ctttattagt tccactgttg c                                              21

<210> SEQ ID NO 38
<211> LENGTH: 21
<212> TYPE: DNA
<213> ORGANISM: Homo sapiens

<400> SEQUENCE: 38
gtgggtagag agaatgagtt t                                              21

<210> SEQ ID NO 39
<211> LENGTH: 21
<212> TYPE: DNA
<213> ORGANISM: Homo sapiens

<400> SEQUENCE: 39
gtgtgtgtta tggacaatta a                                              21

<210> SEQ ID NO 40
<211> LENGTH: 47
<212> TYPE: RNA
<213> ORGANISM: Homo sapiens

<400> SEQUENCE: 40
gcagccguca uuacagcaau ucaagagauu gcuguaauga cggcugc                  47
```

```
<210> SEQ ID NO 41
<211> LENGTH: 57
<212> TYPE: DNA
<213> ORGANISM: Homo sapiens

<400> SEQUENCE: 41
ccgggcagcc gtcattacag caattcaaga gattgctgta atgacggctg ctttttg      57

<210> SEQ ID NO 42
<211> LENGTH: 57
<212> TYPE: DNA
<213> ORGANISM: Homo sapiens

<400> SEQUENCE: 42
aattcaaaaa gcagccgtca ttacagcaat ctcttgaatt gctgtaatga cggctgc      57

<210> SEQ ID NO 43
<211> LENGTH: 57
<212> TYPE: DNA
<213> ORGANISM: Homo sapiens

<400> SEQUENCE: 43
ccggttctcc gaacgtgtca cgtttcaaga gaacgtgaca cgttcggaga atttttg      57

<210> SEQ ID NO 44
<211> LENGTH: 57
<212> TYPE: DNA
<213> ORGANISM: Homo sapiens

<400> SEQUENCE: 44
aattcaaaaa ttctccgaac gtgtcacgtt ctcttgaaac gtgacacgtt cggagaa      57
```

USE OF HUMAN NLK GENE AND ASSOCIATED DRUGS THEREOF

CROSS REFERENCE TO RELATED PATENT APPLICATION

The present application is the US national stage of PCT/CN2012/070537 filed on Jan. 18, 2012, which claims the priorities of the Chinese patent applications No. 201110440594.4 filed on Dec. 23, 2011, which applications are incorporated herein by reference.

BACKGROUND OF THE PRESENT INVENTION

1. Field of Invention

The present invention relates to the field of biotechnology. In particular, it relates to the use of human NLK gene and associated drugs thereof.

2. Description of Related Arts

Nemo-like kinase (Nemo-like kinase, NLK) located in the cell nucleus, is a kind of conserved serine-threonine kinase in the proline-mediated protein kinase superfamily, and is initially considered being relevant to the polarization of eye cells of *drosophila* and the various developmented process of vertebrate (Choi K W et al., *Cell* (1994) 78: 125-36. Verheyen E M et al., *Mech Dev.* (2001) 101: 119-32). The recent studies suggest that NLK can adjust, phosphorylate transcription factors, and involve in apoptosis of cells through various signaling pathways (Brott B K et al., *Proc Natl Acad Sci USA*. (1998) 95: 963-8. Mirkovic I et al., *Mech Dev.* (2002) 119: 9-20).

Wnt signaling transduction pathways include: extracellular factor (Wnt), transmembrane receptors (Frizzled, Fz), cytoplasmic proteins (Dsh, β-catenin/APC/Axin complexes, etc.) and nuclear transcription factor (TCF/LEF), which are closely related to the occurrence and development of various tumors (Bienz M et al., *Cell* (2000) 103: 311-20). NLK is a negative regulator of Wnt/β-catenin signaling pathway, and may phosphorylate TCF/LEF to inhibit the transcriptional activity of β-catenin/TCF complex. C-Myb protein, as the c-myb proto-oncogene expressed product, is deemed as a transcription factor to regulate various downstream gene transcriptions, thereby affecting the proliferation and apoptosis of hematopoietic stem cells. Through transforming growth factor β-activated kinase TAK1, Wnt-1 induces NLK to directly bind with and phosphorylate c-Myb protein at multiple sites, which undergoes subsequently the degradation of ubiquitination and proteasome-dependent, further may cause cell cycle arrest in G1 phase. However, the regulation of a-Myb, which is another member of the Myb family, mainly is the phosphorylation and the inhibition of its binding with the DNA-binding domain to function (Kanei-Ishii C et al., *Genes Dev.* (2004) 18: 816-29). Besides, Research has found that, the phosphorylation of TAK1-NLK pathway has transcription factor FOX01 affecting cell apoptosis, stress, DNA damage/repair and tumorigenesis, and prompts the shift of FOXO1 from the nucleus to the cytoplasm, thereby inhibiting the transcriptional function of FOX01 (Kim S et al., *J Biol Chem*. (2010) 285: 8122-9). Further research has found that, through the phosphorylation of C-terminal region of the transcriptional coactivator factor CBP/P300, NLK further involves in the process of cell apoptosis by way of affecting the transcriptional activity of transcription factors, e.g. NF-κB、AP-1、Smad and the like (Yasuda J et al., *Cancer Sci*. (2004) 95: 52-7. Shi Y et al., *Mol Cell Biochem*. (2010) 333: 293-8).

With respect to the research of NLK in tumor, there have been reports of colorectal cancer, prostate cancer and hepatocellular carcinoma. NLK is considered as a tumor suppressor gene of Wnt/β-catenin signaling pathway in colorectal cancer. Wild-type NLK in colorectal cancer is induced to express, and inhibits cell growth through the phosphorylation of TCF/LEF, and promotes cell apoptosis via p53-independent, but does not affect cell cycle (Yasuda J et al., *Biochem Biophys Res Commun*. (2003) 308: 227-33). In prostate cancer, NLK negatively regulates the signal transduction pathway of androgen receptor. The overexpression of NLK can significantly induce the apoptosis of prostate cancer cell with positive expression of androgen receptor. Further research has found that, by forming complex with androgen receptor, NLK enables the inhibition of androgen receptor from the transcriptional activity of target genes and the depression of androgen receptor mRNA at transcriptional level (Emami K H et al., *Prostate*. (2009) 69: 1481-92). In human hepatic carcinoma cell lines, the knockout of NLK expression can inhibit cell growth. Meanwhile, it is found that, as the increase of G1-S phase cells, the expression of cell cycle-related proteins cyclin D1, CDK2 decreases significantly, which indicates that NLK may give play to the effect of promoting mitosis by acting on cyclin D1、CDK2 in the formation of liver cancer. (Jung K H et al., *J Cell Biochem*. (2010) 110: 687-96). Above all, NLK plays different biological functions during the occurrence and development of different tumors.

RNA interference (RNA interference, RNAi) refers to a short double-stranded RNA (dsRNA) composed of nucleotides performs post-transcriptional gene silencing. It can efficiently and specifically block the expression of certain genes in vivo, cause them to degrade, thereby resulting in the silencing of specific genes in vivo and making cells exhibit a kind of phenotype deletion, which is a rising laboratory technique commonly used to study gene functions and to search a cure for disease in recent years. Research shows that double-stranded RNA with a length of 21-23 nt can specifically cause RNAi at transcription and post-transcriptional level (Tuschl T et al., *Cell* (2000) 101: 25-33). In spite of chemotherapy, radiotherapy, and combination therapy, the five-year survival rate for tumor patients is still quite low. New approaches in tumor treatment could be opened up if the genes relating to the onset and progress of tumors could be subjected to RNA interference. In recent years, RNAi has become an effective strategy for tumor gene therapy. The use of RNAi techniques can inhibit the expression of oncogenes, mutated tumor suppressor genes, cell cycle-related genes, and anti-apoptosis genes and thereby inhibiting the course of tumors (Uprichard et al., *FEBS Letters* (2005) 579: 5996-6007).

In order to further study the regulatory function of NLK in tumorigenesis, the cell models of lung cancer, breast cancer and prostate cancer is selected in the present invention, to study the roles of NLK in the occurrence and development of lung cancer, breast cancer and prostate cancer by means of RNAi.

SUMMARY OF THE PRESENT INVENTION

The object of the present invention is to disclose the therapeutic methods and drugs associated with the human NLK gene.

The first aspect of the present invention discloses a method for inhibiting or reducing tumor cell growth, proliferation, differentiation and/or survival by means of RNA interference, to study the roles of the NLK gene in the occurrence and development of tumor. The method includes: administering molecules to tumor cells, wherein the molecules could specifically inhibit the transcription or translation of the NLK gene, or could specifically inhibit the expression or activity of a NLK protein, so as to inhibit the tumor cell growth, proliferation, differentiation and/or survival.

The tumor cells are selected from the tumor cells, whose growth is relevant with the expression or activity of the NLK protein. Such as any of lung cancer cells, liver cancer cells and breast cancer cells.

In the method for inhibiting or reducing tumor cell growth, proliferation, differentiation and/or survival, the amount of molecules administered is the dosage sufficiently for reducing the transcription or translation of the NLK gene, or for reducing the expression or activity of the NLK protein. The expression of the NLK gene may be at least attenuated by about 50%, 80%, 90%, 95%, or 99%.

The molecules include: a nucleic acid, a carbohydrate, a fat, a small molecule, a polypeptide or a peptide.

The nucleic acids include: an antisense oligonucleotide, a double-stranded RNA (dsRNA), a ribozyme, a RNase III-prepared short interfering RNA (esiRNA) or a short hairpin RNA (shRNA).

The double-stranded RNA, ribozyme, esiRNA or shRNA comprises a promoter sequence of the NLK gene or a message sequence of the NLK gene.

Further, the double-stranded RNA may be a small interfering RNA (siRNA). The small interfering RNA may comprise a sense strand, which may comprise a nucleotide sequence substantially identical to 15-27 consecutive nucleotides of the NLK gene, and an antisense strand, wherein the sense and antisense strands form an RNA duplex. The small molecule interfering RNA can specifically bind the mRNA which is encoded by a target sequence and can specifically silence the expression of a NLK gene.

Further, the sense strand of the small interfering RNA is substantially identical to a target sequence in the NLK gene, the target sequence in the NLK gene comprises a sequence set forth as anyone in SEQ ID NO: 1-39.

The target sequence in the NLK gene refers to the corresponding gene segment in the NLK gene with the mRNA segment, which is in complementary binding with the small molecule interfering RNA, as small molecule interfering RNA specifically silences the expression of the NLK gene.

The shRNA can be expressed via vector, such as expressed after cloning the DNA segment transcripting shRNA into a lentivirus vector.

Preferably, the NLK gene is from human.

The second aspect of the present invention discloses an isolated molecule that attenuates the expression of the NLK gene in tumor cells, which molecule is:

1) a double-stranded RNA comprising a nucleotide sequence that hybridizes under stringent conditions to the NLK gene; or 2) a shRNA comprising a nucleotide sequence that hybridizes under stringent conditions to the NLK gene, or 3) an interference lentivirus vector, which is the lentivirus vector comprising gene segment encoding and expressing the shRNA in 2).

The double-stranded RNA comprises a first strand and a second strand, wherein the first strand is substantially identical to about 15-27 consecutive nucleotides of the NLK gene, and the second strand is substantially complementary to the first strand. Preferably, the first strand is substantially identical to about 19-23 consecutive nucleotides of the NLK gene; more preferably, the first strand is substantially identical to 19, 20, or 21 consecutive nucleotides of the NLK gene.

Further, the double-stranded RNA is small interfering RNA.

The shRNA comprises a sense RNA segment and an antisense RNA segment, wherein the sense RNA segment is substantially identical to about 15-27 consecutive nucleotides of the NLK gene, while the antisense RNA segment is complementary to the sense RNA segment, and the sense RNA segment and the antisense RNA segment are separated by a loop segment. The shRNA becomes small interfering RNA after enzyme digestion, thereby giving a role to specifically silence the expression of endogenous NLK gene in human tumor cells. Preferably, the sense RNA segment is substantially identical to about 19-23 consecutive nucleotides of the NLK gene; more preferably, the sense RNA segment is substantially identical to 19, 20 or 21 consecutive nucleotides of the NLK gene.

The loop segment may comprise a sequence selected from the group consisting of UUCAAGAGA, AUG, CCC, UUCG, CCACC, CTCGAG, AAGCUU and CCACACC.

The first strand of the double-stranded RNA or the sense RNA segment of the shRNA is substantially identical to a target sequence in the NLK gene.

Preferably, the target sequence in the NLK gene comprises a sequence set forth as anyone in SEQ ID NOs: 1-39.

Preferably, the NLK gene is from human.

In some embodiments of the present invention, the sequence in shRNA comprises SEQ ID NO: 40.

GCAGCCGUCAUUACAGCAAUUCAAGAGAUUGCUGUAAUGACGGCUGC

The NLK gene interference lentivirus vector is obtained by cloning the DNA segment encoding the said shRNA into a lentivirus vector The NLK gene interference lentivirus vector can be packaged by a lentivirus into a infectious lentivirus particles, thereby infecting tumor cells and transcribing the shRNA.

The NLK gene interference lentivirus vector further comprises a promoter sequence and/or a nucleotide sequence encoding a detectable marker in the tumor cell. The detectable marker may be a green fluorescent protein (GFP).

Further, the lentivirus vector may be selected from the group consisting of pLKO.1-puro, pLKO.1-CMV-tGFP, pLKO.1-puro-CMV-tGFP, pLKO.1-CMV-Neo, pLKO.1-Neo, pLKO.1-Neo-CMV-tGFP, pLKO.1-puro-CMV-TagCFP, pLKO.1-puro-CMV-TagYFP, pLKO.1-puro-CMV-TagRFP, pLKO.1-puro-CMV-TagFP635, pLKO.1-puro-UbC-TurboGFP, pLKO.1-puro-UbC-TagFP635, pLKO-puro-IPTG-1xLacO, pLKO-puro-IPTG-3xLacO, pLP1, pLP2, pLP/VSV-G, pENTR/U6, pLenti6/BLOCK-iT-DEST, pLenti6-GW/U6-laminshrna, pcDNA1.2/V5-GW/lacZ, pLenti6.2/N-Lumio/V5-DEST, pGCSIL-GFP and Lenti6.2/N-Lumio/V5-GW/lacZ.

The isolated molecule may be used to prepare drugs for preventing or treating tumor. Further, the tumor is selected from the group consisting of lung cancer, breast cancer and prostate cancer.

When used as drugs or preparation for treating tumors, a therapeutically effective amount of double-stranded RNA or shRNA is administered to a mammalian subject. The specific dosage should be determined by a skilled physician by considering administration strategy and patient healthy conditions.

The third aspect of the present invention discloses an isolated target oligonucleotide segment, which is an isolated molecule target oligonucleotide segment for attenuating the expression of a NLK gene in a tumor cell, the oligonucleotide sequence may comprise the nucleotide sequence set forth as anyone in SEQ ID NO: 1-39.

The target oligonucleotide segment may be used for screening drugs or preparation for treating tumors.

Specifically, the drugs or preparation may be screened by using the target oligonucleotide segment as the target object, to find out the drugs which could specifically attenuate or promote the expression of human NLK gene as candidate drugs for treating tumors. For example, the small molecule interfering RNA obtained by screening can be used as a drug which could specifically inhibit tumor cell proliferation. Such as antibody drugs, small molecule drugs and the like, can also use target oligonucleotide segment as target object.

The fourth aspect of the present invention discloses a NLK interference lentivirus, which is obtained after cloning lentivirus vector into the nucleotide segment being transcribed to shRNA in tumor cells, and by means of packaging the lentivirus vectors with the auxiliary of lentivirus packaging plasmid and certain cell lines. The lentivirus can infect tumor cells and produce the small molecule interfering RNA for specifically silencing the NLK gene, thereby inhibiting the proliferation of tumor cells.

The NLK interference lentivirus can be used to prepare drugs for preventing or treating tumor. Further, the tumor is selected from the group consisting of lung cancer, breast cancer and prostate cancer.

The fifth aspect of the present invention discloses a pharmaceutical composition for preventing or treating tumor, the pharmaceutical composition comprises the isolated molecule or a NLK interference lentivirus that attenuates expression of a NLK gene.

The pharmaceutical composition further comprises a pharmaceutically acceptable carrier or excipient.

During preparation of the pharmaceutical composition, the active ingredients are generally mixed with an excipient or are diluted with an excipient or are wrapped in a carrier that can exist in the form of a capsule or a medicine bag. When the excipient acts as a diluent, it can serve as a solid, semi-solid, or liquid medium for the excipient, carrier, or active ingredients. Therefore, the pharmaceutical composition may be in the form of tablets, pills, powder, solution, syrup, or sterile injection solutions. Examples of suitable excipients include lactose, glucose, sucrose, sorbitol, mannitol, starch, microcrystalline cellulose, polyvinyl pyrrolidone, cellulose, and water. Preparations may further include: wetting agents, emulsifiers, preservatives (such as hydroxyl benzoic acid methyl ester and propyl ester), and sweeteners.

The sixth aspect of the present invention discloses a method for preventing or treating tumor in a subject, which method includes administering an effective amount of the pharmaceutical composition into the subject.

The tumor is selected from the group consisting of lung cancer, breast cancer and prostate cancer.

By employing this method, the growth, proliferation, recurrence and/or metastasis of the tumor may be inhibited. Further, the growth, proliferation, recurrence and/or metastasis of the tumor may be inhibited by at least 10%, 20%, 30%, 40%, 50%, 60%, 70%, 80%, 90%, 95% or 99%.

Further, the subject employing the method is human.

The seventh aspect of the present invention discloses a kit for attenuating the expression of a NLK gene in tumor cells, which kit includes the isolated molecule or the NLK interference lentivirus in a container.

The present invention designs 39 RNAi target sequence on human NLK gene and constructs a corresponding NLK RNAi vector, wherein the RNAi vector pGCSIL-GFP-siNLK in the encoding sequence as set forth in SEQ ID NO 20 could obviously attenuate expression of a NLK mRNA and NLK protein. The lentivirus (simplified as 'Lv') is adopted as gene operation tool to carry the RNAi vector pGCSIL-GFP-siNLK into tumor cells, such as human lung cancer H1299 cells, breast cancer MCF-7 cells, and prostate cancer PC-3 cells, in order to introduce the human NLK RNAi sequence into those tumor cells effectively and specifically, thereby attenuating expression of NLK gene and significantly inhibiting proliferation of the above-described tumor cells. Therefore, the lentiviral-vector-mediated NLK gene silence is a potential clinic non-operative therapy.

The isolated molecule or a NLK interference lentivirus that attenuates expression of a NLK gene provided in the present invention can specifically attenuates expression of human NLK, especially the lentivirus, can effectively infect target cells, efficiently inhibit NLK expression in target cells, and inhibit the growth of tumor cells, thus has great significance in tumor treatment.

DETAILED DESCRIPTION OF THE PREFERRED EMBODIMENTS

Figure 1:
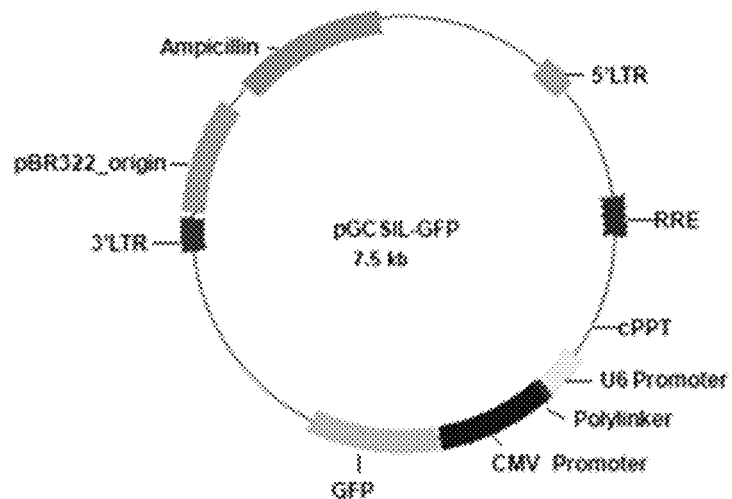
FIG. 1 shows DNA profiles of a pGCSIL-GFP plasmid.

The present invention relates to the discovery that the use of the RNAi method can, after lowering the expression of the NLK gene in human tumor cells, effectively inhibit the proliferation of tumor cells. Thus, it is proved that the NLK gene is an oncogene and can be a target for tumor treatment. Further, a series of siRNA sequences that interfere with NLK gene were synthesized and tested to screen the siRNA which can, after lowering the expression of NLK gene, effectively inhibit the proliferation and growth of tumor cells, such as human lung cancer H1299 cells, breast cancer MCF-7 cells, and prostate cancer PC-3 cells. The present invention was completed based on the above-described research.

The present invention provides a series of small interfering RNA (siRNA) sequences interfering human NLK gene and constructs a lentivirus which could specifically silence NLK gene expression. It has been found in the present invention, the small interfering RNA and RNAi lentivirus designed for human NLK gene could attenuate the expression of NLK gene stably and specifically and effectively inhibit the proliferation of human tumor cells. It was demonstrated in the present invention that the NLK gene could promote the growth of tumor cells and possibly be used as target for early diagnosis and treatment of tumors. Besides, it could be an effective approach to inhibit tumor development via silencing the expression of NLK gene by RNA interference.

The principles of the present invention are as follows.

A human NLK gene RNAi lentivirus is obtained via the following method: obtaining human NLK genetic coding sequence from Genbank, predicting siRNA locus, designing effective siRNA sequence for the NLK gene; synthesizing Oligo DNA of target sequence and forming double-stranded DNA by annealing, producing a short hairpin RNA lentivirus plasmid after linking to the lentiviral vector being enzyme digested by Age I and EcoR I restriction enzyme; the screening effective short hairpin RNA lentivirus plasmid and the auxiliary vectors (Packing Mix, Sigma-Aldrich company) required for lentiviral packaging are jointly transfected onto 293T cells for packaging the recombinant lentiviruse for expressing NLK gene. Thus, pure and stable expression NLK siRNA lentiviruse (Lv-siNLK) is produced by collecting the lentiviruses particles in cell culture supernatant and purifying and condensing.

According to the above method, the present invention provides 39 effective targets for interfering NLK gene (specifically as set forth in SEQ ID NO 1-39), and constructs lentivirus for specific interfering human NLK gene.

At the same time, the present invention further discloses a RNAi lentivirus for human NLK gene and its preparation and usage.

In the present invention, it has been found that RNAi approach mediated by lentivirus could, after lowering the expression of the NLK gene in tumor cells, effectively inhibit the proliferation and growth of tumor cells. It has been demonstrated that NLK gene, as an oncogene, which would promote tumor proliferation, has been verified as having important physiological functions during the occurrence and development of tumors. Therefore, the NLK gene could be a target during tumor treatment, and specific silence of NLK gene mediated by lentivirus may be a new approach for tumor treatment.

The implementation of the present invention is described below through specific embodiments. It can be understood that the embodiments are used to describe the invention, but are not intended to limit the scope of the invention. In the embodiments, the experimental method without specifying specific conditions and reagents without formula are well known to those of skill in the art and are described, for example, in Sambrook et al, *Molecular Cloning: A Laboratory Manual*, 3rd ed., (Science Press, BeiJing. 2002), or the protocols provided by the manufacturers.

First Embodiment

Preparation of RNAi Lentivirus for Human NLK Gene

1. Constructing RNAi Lentivirus for Human NLK Gene

NLK (NM_016231) genetic information is obtained from Genbank. Genechem™ (Shanghai Genechem Co., Ltd.) is used to design effective siRNA targets for the NLK gene. In the NLK gene coding sequence (CDS) region, 19-21 base sequences starting with every other base are determined Table 1 lists the 39 effective siRNA target sequences for the NLK gene.

TABLE 1 siRNA target sequences of the human NLK

| SEQ ID NO | Target Sequence | GC % |
|---|---|---|
| 1 | TACAGTTAAGGCGCACCATCA | 47.62% |
| 2 | CACCATCATCAGCACTCGCAT | 52.38% |
| 3 | CAGCTGGATATTGAGCCGGAT | 52.38% |
| 4 | CGGATAGACCTATTGGATATG | 42.86% |
| 5 | GACCTATTGGATATGGAGCCT | 47.62% |
| 6 | TTGGTGTTGTCTGGTCAGTAA | 42.85% |
| 7 | TGGTGTTGTCTGGTCAGTAAC | 47.62% |
| 8 | AAGGGTCTTCCGGGAATTGAA | 47.62% |
| 9 | CGGGAATTGAAGATGTTGTGT | 42.86% |
| 10 | AAGCATGATAATGTACTCTCT | 33.33% |
| 11 | AACCTCCACACATTGACTATT | 38.10% |
| 12 | CACAGAATTGATGCAGAGTGA | 42.86% |
| 13 | AACCACTCAGCTCAGATCATG | 47.62% |
| 14 | GCTCAGATCATGTCAAAGTTT | 38.10% |
| 15 | TATCTCCATTCAGCTGGCATT | 42.86% |
| 16 | GCAACTGTGTTCTAAAGATTT | 33.33% |
| 17 | AACTGTGTTCTAAAGATTTGT | 28.57% |
| 18 | CAGGAAGTTGTTACTCAGTAT | 38.10% |
| 19 | AGGAAGTTGTTACTCAGTATT | 33.33% |
| 20 | GCAGCCGTCATTACAGCAA | 52.63% |
| 21 | TGCAGAACTACTAGGACGAAG | 47.62% |
| 22 | AGAACTACTAGGACGAAGAAT | 38.10% |
| 23 | GAACTACTAGGACGAAGAATA | 38.10% |
| 24 | AACTACTAGGACGAAGAATAT | 33.33% |
| 25 | CACACCATCACTGGAAGCAAT | 47.62% |
| 26 | TGAAGGCGCTAAGGCACATAT | 47.62% |
| 27 | GAAGGCGCTAAGGCACATATA | 47.62% |
| 28 | AACAGCCATCTCTTCCTGTAC | 47.62% |
| 29 | CAGGCTACACATGAAGCTGTT | 47.62% |
| 30 | AAGCTGTTCATCTCCTTTGCA | 42.86% |
| 31 | CTTTGCAGGATGTTGGTCTTT | 42.86% |
| 32 | TGCAGGATGTTGGTCTTTGAT | 42.86% |
| 33 | GACTTTGAGCCTGTCACCAAT | 47.62% |
| 34 | GAGCCTGTCACCAATCCCAAA | 52.38% |
| 35 | AAGAGCTTTATTAGTTCCACT | 33.33% |
| 36 | GAGCTTTATTAGTTCCACTGT | 38.10% |
| 37 | CTTTATTAGTTCCACTGTTGC | 38.10% |

TABLE 1-continued siRNA target sequences of the human NLK

| SEQ ID NO | Target Sequence | GC % |
|---|---|---|
| 38 | GTGGGTAGAGAGAATGAGTTT | 42.86% |
| 39 | GTGTGTGTTATGGACAATTAA | 33.33% |

A single-stranded DNA oligo sequence is synthesized for an siRNA target (e.g., SEQ ID NO 20), which further forms a double-stranded DNA oligo that respectively contains sticky-ended Age I and EcoRI enzyme digesting sites at two ends by means of annealing (Table 2). The Age I and EcoRI restriction enzymes are used on the pGCSIL-GFP vector (Shanghai Genechem Co., Ltd.; as shown in FIG. 1) to linearize it; the enzyme digestion segments are identified using agarose gel electrophoresis.

TABLE 2

Double-stranded DNA oligo that respectively contains sticky-ended Age I and EcoRI enzyme degesting sites at two ends

| No. | 5' | Neck | Loop | Neck | 3' |
|---|---|---|---|---|---|
| Sense strand | CCGG | GCAGCCGTCA TTACAGCAA | TTCAAGA GA | TTGCTGTAATGA CGGCTGC | TTTT TG |
| Anti-sense strand | AATT CAAA AA | GCAGCCGTCA TTACAGCAA | TCTCTTG AA | TTGCTGTAATGA CGGCTGC | |

The pGCSIL-GFP plasmid is enzyme digested by the Age I and EcoRI restriction enzymes and linearizes. The reaction system is shown in table 3 with the reaction condition: 37° C., 1 h.

TABLE 3

Enzyme digestion reaction system for pGCSIL-GFP plasmid

| Reagent | Volume (μl) |
|---|---|
| pGCSIL-GFP plasmid (1 μg/μl) | 2 |
| buffer (10x) | 5 |
| BSA (100x) | 0.5 |
| Age I (10 U/μl) | 1 |
| EcoR I (10 U/μl) | 1 |
| H$_2$O | 40.5 |
| Total | 50 |

The vector DNA is ligated to the purified double-stranded DNA Oligo by T4 DNA ligase in an appropriate buffer system. The ligation system is shown in table 4 with the reaction condition: 16° C., 12 h.

TABLE 4

Ligation system

| Reagent | Positive control (μl) | Self-ligation control (μl) | Ligation group (μl) |
|---|---|---|---|
| Linearized vector DNA (100 ng/μl) | 1 | 1 | 1 |
| Annealed double-stranded DNA Oligo (100 ng/μl) | 1 | — | 1 |
| T4 bacteriophage DNA ligase buffer solution (10x) | 1 | 1 | 1 |
| T4 bacteriophage DNA ligase | 1 | 1 | 1 |
| dd H$_2$O | 16 | 17 | 16 |
| Total | 20 | 20 | 20 |

The ligation products are used to transform fresh *E. coli* competent cells that had been prepared with calcium chloride (for the transformation procedure, reference: Molecular Cloning: A Laboratory Manual, 2nd ed., supra at pp. 55-56). The bacterial clone surface grown from the ligation-transformation products is picked and dissolved in 10 μl LB culture medium, mixed, and 1 μl is drawn as a template. General PCR primers (forward primer sequence: 5'-CCTATTTCCCAT-GATTCCTTCATA-3; reverse primer sequence: 5'-GTAATACGGTTATCCACGCG-3') upstream and downstream of the RNAi sequence in the lentiviral vector are designed, to perform PCR amplication tests. The PCR reaction system is as shown in Table 5, and the cyclic conditions are as shown in Table 6.

TABLE 5

PCR reaction system

| Reagent | Volume (μl) |
|---|---|
| Buffer (10x) | 2 |
| dNTPs (2.5 mM) | 0.8 |
| Forward primer | 0.4 |
| Reverse primer | 0.4 |
| Taq polymerase | 0.2 |
| Template | 1 |
| ddH$_2$O | 15.2 |
| Total | 20 |

TABLE 6

The cyclic conditions of PCR reaction

| 1 Cycle | 30 Cycles | | | 1 Cycle |
|---|---|---|---|---|
| 94° C. 30 s | 94° C. 30 s | 55° C. 30 s | 72° C. 30 s | 72° C. 6 min |

PCR amplication products are identified using agarose gel electrophoresis, and sequencing and sequence alignment analysis are performed on clones with positive PCR identifications. Correctly aligned clones are successfully constructed as RNAi vectors containing NLK-siRNA-20 (SEQ ID NO 20 in Table 1) and named as pGCSIL-GFP-siNLK.

A pGCSIL-GFP-siScr plasmid is constructed as negative control, RNAi negative control siRNA target sequence is 5'-TTCTCCGAACGTGTCACGT-3', which is not homologous with any sequence in human gene group compared to GenBank. When the pGCSIL-GFP-siScr scrambled plasmid is constructed, a double-stranded DNA oligo sequence that respectively contains sticky-ended Age I and EcoR I enzyme digestion sites at two ends is synthesized for the Scr (scramble) siRNA target (Table 7). The remaining methods of construction and methods and conditions of identification are the same as for pGCSIL-GFP-siNLK.

TABLE 7

Double-stranded DNA oligo that contains sticky-ended Age I and EcoR I enzyme digestion sites at both ends

| | 5' | Neck | Loop | Neck | 3' |
|---|---|---|---|---|---|
| Sense strand | CCGG | TTCTCCGAAC GTGTCACGT | TTCAAGAGA | ACGTGACACG TTCGGAGAA | TTTTTG |
| Anti-sense strand | AATT CAAA AA | TTCTCCGAAC GTGTCACGT | TCTCTTGAA | ACGTGACACG TTCGGAGAA | |

2. Packaging RNAi Lentivirus for Human NLK Gene (Lv-siNLK)

The DNA of the RNAi plasmid pGCSIL-GFP-siNLK is extracted using Qiagen's plasmid extraction reagent kit and is used to prepare 100 ng/μl storage solution. 24 hours prior to transfection, pancreatic enzyme digestion is performed on 293T cells in the logarithmic growth phase. Using DMEM complete culture medium containing 10% fetal bovine serum, the cell density is adjusted to $1.5 \times 10^5$ cells/ml; cells are inoculated onto a 6-well plate at 37° C. and cultivate in a 5% $CO_2$ culture box. It is used for transfection as soon as cell density reached 70%-80%. Two hours prior to transfection, the original culture medium is removed, and 1.5 ml fresh, complete culture medium is added. In accordance with the instructions for Sigma-Aldrich's MISSION Lentiviral Packaging Mix™ reagent kit, Packing Mix (PVM) 20 μl, PEI 12 μl, and serum-free DMEM culture 400 μl are added into a sterilized centrifuge tube. 20 μl of the above-described extracted plasmid DNA is added to the above-described PVM/PEI/DMEM mixture. The above-described transfection mixture is incubated at room temperature for 15 minutes, and transferred into a culture medium of 293T cells, and cultured at 37° C. in a 5% $CO_2$ culture box for 16 hours. The culture medium containing the transfection mixture is discarded, the cells are washed with PBS solution, and added with complete culture medium 2 ml, and cultured for 48 hours. The cell supernatant fluid is collected, purified with a Centricon Plus-2™ centrifugal filter (Millipore), and the lentiviruses are concentrated. The following steps are performed: (1) 4° C., centrifuge at 4,000 g for 10 min, and remove cell debris; (2) filter supernatant with 0.45 μm filter in a 40 ml ultrafast centrifuge tube; (3) centrifuge at 4,000 g for 10-15 min until the desired volume of viral concentrate is reached; (4) after centrifuging ends, separate the filtration cup and the cup for collecting filtrate, turn the filtration cup upside down onto the sample collection cup, centrifuge for 2 min, keeping centrifugal force at a maximum of 1,000 g; (5) remove the centrifuge cup from the sample collection cup. The sample collection cup contains lentiviral Lv-siNLK concentrate. The titer of lentiviral concentrate is measured and packed in separate containers and stores at −80° C. The packaging and purified process for negative control RNAi lentiviruses (Lv-siScr) is the same as for the Lv-siNLK lentiviruse, except that pGCSIL-GFP-siScr vector is substituted for pGC-SIL-GFP-siNLK vector.

Second Embodiment

NLK Gene Silencing Efficiency as Measured by Real-Time Fluorescent Quantitative RT-PCR Pancreatic enzyme digestion is performed on human lung cancer H1299 cells, breast cancer MCF-7 cells, and prostate cancer PC-3 cells in logarithmic growth phase, to prepare a cellular suspension (cell count of roughly $5 \times 10^4$/ml); cells are inoculated into a 6-well plate, and cultivated until a cell confluence of approximately 30% is reached. In accordance with the multiplicity of infection (MOI) value, a suitable quantity of viruses (MOI of H1299=10, MOI of PC-3 and MCF-7=20) are added. After culturing for 24 h, the culture medium is replaced. Cells are collected after 5 days of infection. Total RNA is extracted in accordance with Invitrogen's Trizol™ operating manual. cDNA is produced by reverse transcription of RNA in accordance with Promega's M-MLVT™ operating manual. The reaction system is shown in Table 8 with reaction condition: react in 42° C. for 1 hour, followed by bathing 10 min at 70° C. in a water bath to deactivate the reverse transcriptase.

TABLE 8

Reverse transcription reaction system

| Reagent | Volume (μl) |
|---|---|
| RT buffer (5×) | 4 |
| 10 mM dNTPs | 2 |
| RNasin | 0.5 |
| M-MLV-RTase | 1 |
| DEPC $H_2O$ | 3.5 |
| Total | 11 |

The primer sequence of NLK gene is as follows: forward primer is 5'-ATCATCAGCACTCGCATCATC-3', while reverse primer is 5'-GACCAGACAACACCAAAGGC-3'. Using the housekeeping gene GAPDH as an internal reference, the primer sequence is as follows: forward primer is 5'-TGACTTCAACAGCGACACCCA-3', while reverse primer is 5'-CACCCTGTTGCTGTAGCCAAA-3'. A TP800™ real time PCR instrument (TAKARA) is used to conduct real-time quantitative measurement, the reaction system is shown in Table 9. The reaction procedure is set as follows: pre-denaturation 95° C., 15 s; thereafter, each step denaturation at 95° C., 5 s; annealing extension 60° C., 30 s; total of 45 cycles. The absorbance value in each extension phase is read.

TABLE 9

Real-time PCR reaction system

| Reagent | Volume (μl) |
|---|---|
| SYBR premix ex taq: | 10 |
| Forward primer (2.5 μM) | 0.5 |
| Reverse primer (2.5 μM) | 0.5 |
| cDNA | 1.0 |
| dd$H_2O$ | 8.0 |
| Total | 20 |

Figure 2:
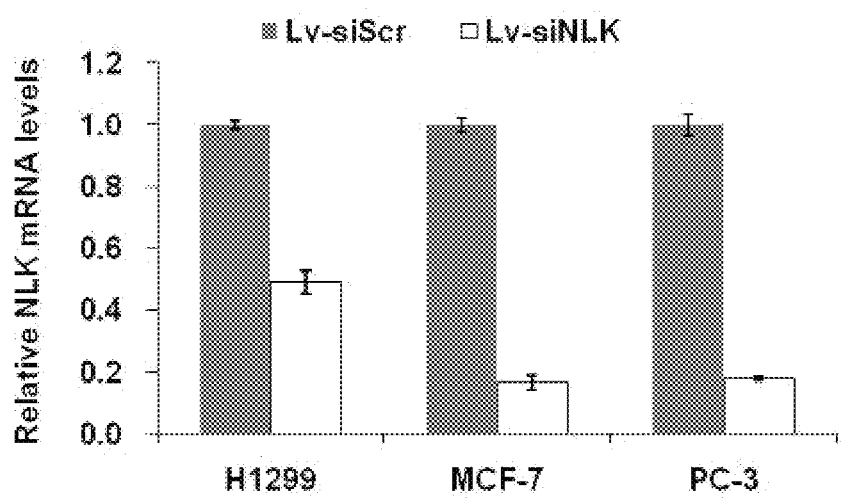
FIG. 2 shows significantly decreased NLK mRNA expression level 5 days after Lv-siNLK lentiviruse infection of human lung cancer H1299 cells, breast cancer MCF-7 cells, and prostate cancer PC-3 cells.

PCR is followed by denaturation at 95° C. for 1 min; then cools to 55° C. to bind double-standard DNA sufficiently. Temperature is changed in increments of 0.5° C. from 55° C. to 95° C., maintaining for 4 s at each step. At the same time, absorbance readings are taken and a melting curve is produced. The $2^{-\Delta\Delta Ct}$ analytic method is used to calculate the expression abundance of infected NLK mRNA. Compared to cells infected with the control lentivirus (Lv-siScr), test results show that the expression of NLK mRNA in human lung cancer H1299 cells, breast cancer MCF-7 cells, and prostate cancer PC-3 cells drops 50.8%, 83.4% and 82.1%, respectively (FIG. 2).

Third Embodiment

Figure 3:
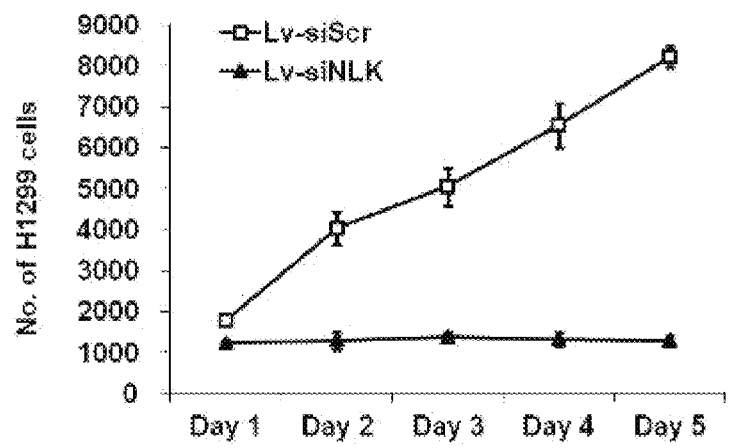
FIG. 3 shows that, 5 days after infecting human lung cancer H1299 cells, Lv-siNLK lentiviruse cause inhibition of cell proliferation.
Figure 4:
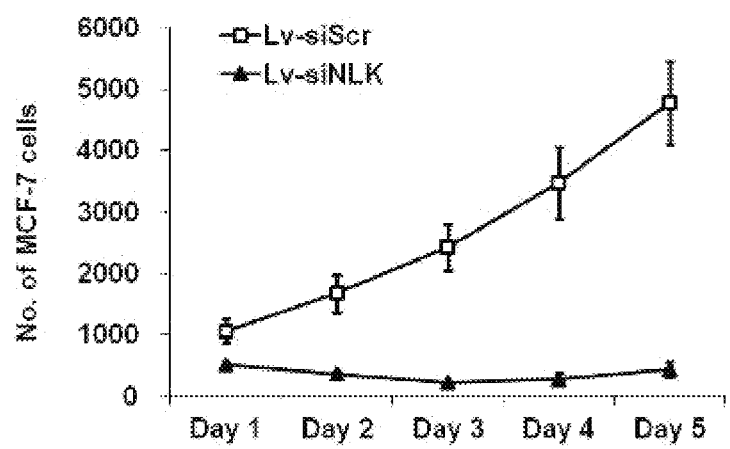
FIG. 4 shows that, 5 days after infecting human breast cancer MCF-7 cells, Lv-siNLK lentiviruse cause inhibition of cell proliferation.
Figure 5:
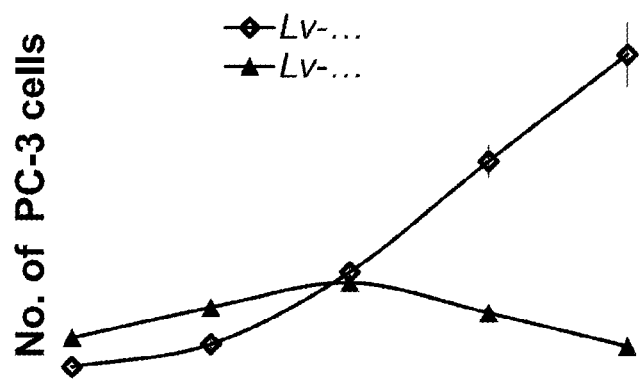
FIG. 5 shows that, 5 days after infecting human prostate cancer PC-3 cells, Lv-siNLK lentiviruse cause inhibition of cell proliferation.

Measurement of the Proliferation Capacity of Tumor Cells Infected with Lv-siNLK Lentivirus Pancreatic enzyme digestion is performed on human lung cancer H1299 cells, breast cancer MCF-7 cells, and prostate cancer PC-3 cells in logarithmic growth phase, to prepare a cellular suspension (cell count of roughly $5 \times 10^4$/ml); cells are inoculated into a 6-well plate, and cultivated until a cell confluence of approximately 30% is reached. In accordance with the multiplicity of infection (MOI) value, a suitable quantity of viruses (MOI of H1299=10, MOI of PC-3 and MCF-7=20) are added. After culturing for 24 h, the culture medium is replaced. After 5 days of infection time, cells are collected from each test group while in the logarithmic growth phase. The cells are resuspended in complete culture medium to form a cell suspension ($2 \times 10^4$/ml) and inoculated in a 96-well plate at a cell density of 2,000/well. Each group is repeated in 5 wells, with 100 μl per well. After filling the plate, the cells are cultured in a 5% $CO_2$ culture box set at 37° C. Beginning on the second day after filling the plate, the plate is read once daily using a Cellomics ArrayScan VTI (Thermo Scientific) device for five consecutive days. By adjusting the input parameters of the Cellomics™ device, the enhanced green fluorescent cell count per plate scan is calculated. The data are used to plot a statistical graph and cell proliferation curve (shown in FIGS. 3-5). The results indicate that, five days after in vitro culturing of Lv-siNLK lentivirus-infected, the viable cells of human lung cancer H1299 cells, breast cancer MCF-7 cells, and prostate cancer PC-3 cells drops 84.4%, 91.0% and 88.5%, respectively, which demonstrates that NLK gene silence leads to the inhibition of the proliferation ability of the tumor cells.

Fourth Embodiment

Testing NLK Gene Overexpression in Tumor Cells

Figure 6:
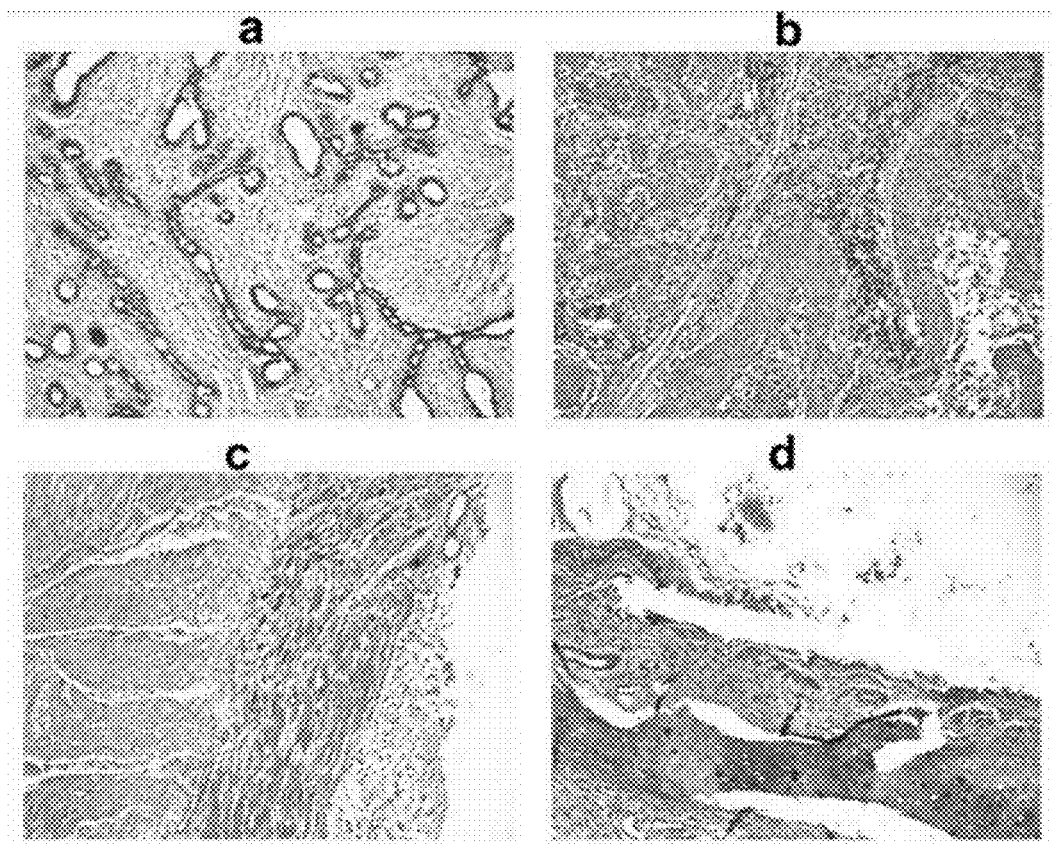
FIG. 6 shows immunohistochemical staining using anti-NLK antibodies on human tumor tissues: a is breast cancer; b, c, d are lung cancer

Tissue samples used are from human breast cancer and lung cancer.
NLK antibody: from Sigma™
Test Method:
A tissue microarray is put in a 60° C. incubator and heated for 30 minutes. Then the tissue microarray is dewaxed. The dewaxing process is as follows: dimethyl benzene 15 minutes; soak 10 minutes in sequence: in dimethyl benzene:ethanol=1:1 mixture, in absolute alcohol, in 95% ethanol, in 85% ethanol, in 75% ethanol, and in distilled water; then use distilled water or PBS to prepare fresh 3% $H_2O_2$, and seal for 10 minutes at room temperature. For antigen retrieval, 0.01 M sodium citrate buffer solution (pH 6.0) is heated on high heat until it boils; then the tissue microarray is placed in the solution and heated for 20 minutes on low heat. After cooling naturally to room temperature, the tissue microarray is set in distilled water and soaked for 10 minutes; sealed with 10% serum (TBS preparation) for 30 minutes; serum is discarded, and without washing, NLK antibody (1:100 dilution) is added and incubated overnight. The tissue microarray is washed with TBS twice, each time for 5 minutes; HRP-labeled goat anti-rabbit secondary antibodies are added and incubated at room temperature for 60 minutes; washed with TBS four times, each time for 5 minutes. DAB dye is added until light yellow appeared. The tissue microarray is placed in distilled water to terminate reaction; soaked in hematoxylin for 30 seconds; rinsed with clear water 7 or 8 times; dehydrated and mounted; soaked 5 minutes in sequence: 75% ethanol, 85% ethanol, 95% ethanol, absolute ethanol, dimethyl benzene:ethanol=1:1 mixture, and dimethyl benzene. 30 ul neutral plastic is dipped onto the tissue microarray and mounted with cover glass, dried by airing, and observed and photographed (results shown in FIG. 6).
The Results Indicate:
NLK antibodies are used to conduct immunohistochemical expression tests on different tumor tissues. The results show high expression of nlk gene-coded proteins in human breast cancer and lung cancer tissue samples. Brown color in figure represents positive expression. Therefore, based on the results of this experiment, that detection of nlk gene expression of histocyte can be used for the auxiliary diagnosis of cancer.

Fifth Embodiment

Figure 7:
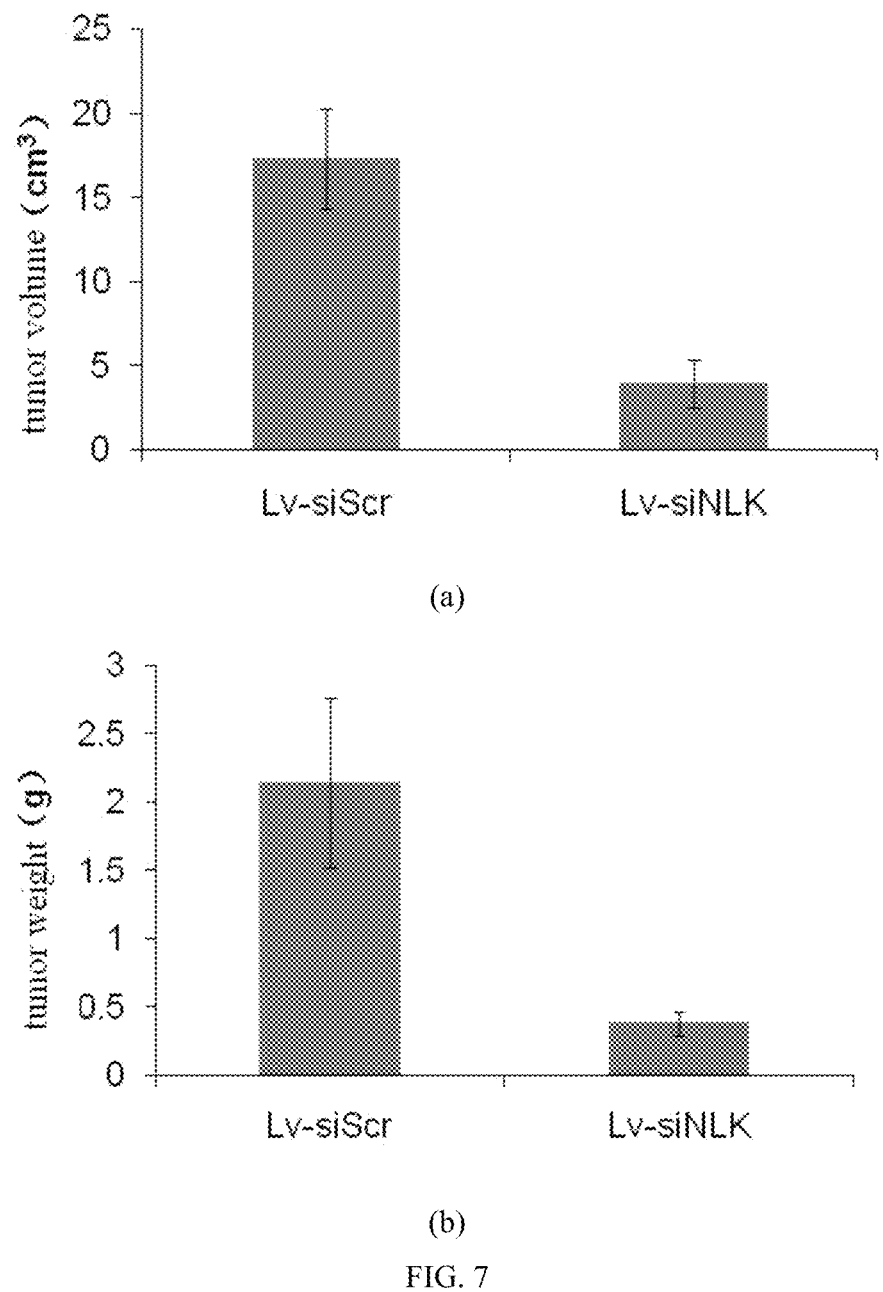
FIG. 7 shows in vivo tumorigenic ability experiment results of tumor cells infected by Lv-siNLK lentiviruse:
a. tumor volume, b. tumor weight

In Vivo Tumorigenic Ability of Lentivirus-Infected Tumor Cells Infected with Lv-siNLK Lentivirus Pancreatic enzyme digestion is performed on human breast cancer MCF-7 cells in logarithmic growth phase, to prepare a cellular suspension (cell count of roughly $5 \times 10^4$/ml); cells are inoculated into a 6-well plate, and cultivated until a cell confluence of approximately 30% is reached. In accordance with the multiplicity of infection (MOI: 20), a suitable quantity of viruses are added. After culturing for 24 h, the culture medium is replaced. After 5 days of infection time, cells from each test group and cells from the control groups while both in the logarithmic growth phase, are collected respectively. The cells are resuspended in complete culture medium to form a cell suspension which is injected into the right armpit of 5 to 6 weeks old female BALB/c nude mice ($2 \times 10^6$ cells per mouse). MCF-7 cells infected with Lv-siNLK lentivirus is injected into the mice of the test group, while MCF-7 cells infected with Lv-siScr lentivirus is injected into the mice of the control group. Each group includes six nude mice. After the injection, the nude mice are fed until visible tumor appeared (about one week), and the volume (as shown in FIG. 7a) and weight (as shown in FIG. 7a) of tumors are measured by NightOWL II 983 spectroscopic imaging system (Berthold Technologies). The results indicate that the tumorigenic ability of the test group is much higher than that of the control group. According to such result, it believes that Lv-siNLK could inhibit the proliferation of tumor cells in vivo.

What is claimed is:

1. A method for inhibiting or reducing tumor cell growth, proliferation, differentiation and/or survival, which method includes: administering molecules to tumor cells, wherein the molecules specifically inhibit the transcription or translation of a Nemo-like kinase gene, or specifically inhibit the expression or activity of a Nemo-like kinase protein, to inhibit the tumor cell growth, proliferation, differentiation and/or survival, wherein the molecule is a nucleic acid targeted to SEQ ID NOs: 1-39 or the molecule is a shRNA comprising SEQ ID NO:40.

2. The method according to claim 1, characterized in that, the nucleic acid includes: an antisense oligonucleotide, a double-stranded RNA, a ribozyme, an esiRNA or a shRNA.

3. The method according to claim 2, characterized in that, the double-stranded RNA, ribozyme, esiRNA or shRNA comprises a promoter sequence of the Nemo-like kinase gene or a message sequence of the Nemo-like kinase gene.

4. The method according to claim 3, characterized in that, the double-stranded RNA is a small interfering RNA.

5. The method according to claim 4, characterized in that, the small interfering RNA comprises a sense strand and an antisense strand, the sense strand comprises a nucleotide sequence substantially identical to 15-27 consecutive nucleotides of the Nemo-like kinase gene, and the sense and the antisense strands form an RNA duplex.

6. The method according to claim 5, characterized in that, the sense strand of the small interfering RNA is substantially identical to a target sequence in the Nemo-like kinase gene; the target sequence in the Nemo-like kinase gene comprises a sequence set forth as anyone in SEQ ID NO: 1-39.

7. The method according to claim 1, characterized in that, the Nemo-like kinase gene is from human.

8. The method according to claim 1, characterized in that, the tumor cells are selected from the tumor cells, whose growth is relevant with the expression or activity of the Nemo-like kinase protein.

9. The method according to claim 8, characterized in that, the tumor cells are selected from the group consisting of lung cancer, breast cancer and prostate cancer.

10. The method according to claim 1, characterized in that, the amount of molecules administered is the dosage sufficiently for reducing the transcription or translation of the Nemo-like kinase gene, or for reducing the expression or activity of the Nemo-like kinase protein.

11. The method according to claim 10, characterized in that, the expression of Nemo-like kinase genes is at least attenuated by 50%, 80%, 90%, 95%, or 99%.

12. The method according to claim 1, characterized in that the administering molecule is:
  a) a double-stranded RNA comprising a nucleotide sequence that hybridizes under stringent conditions to the Nemo-like kinase gene; or
  b) a shRNA comprising a nucleotide sequence that hybridizes under stringent conditions to the Nemo-like kinase gene, or
  c) an interference lentivirus vector, which is the lentivirus vector comprising gene segment encoding and expressing the shRNA in b).

13. The method according to claim 12, characterized in that:
  the double-stranded RNA comprises a first strand and a second strand, wherein the first strand is substantially identical to about 15-27 consecutive nucleotides of the Nemo-like kinase gene, and the second strand is substantially complementary to the first strand;

the shRNA comprises a sense RNA segment and an antisense RNA segment, wherein the sense RNA segment is substantially identical to about 15-27 consecutive nucleotides of the Nemo-like kinase gene, while the antisense RNA segment is complementary to the sense RNA segment, and the sense RNA segment and the antisense RNA segment are separated by a loop segment.

14. The method according to claim 13, characterized in that, the Nemo-like kinase gene is from human.

15. The method according to claim 13, characterized in that, the loop segment comprises a sequence selected from the group consisting of UUCAAGAGA, AUG, CCC, UUCG, CCACC, CTCGAG, AAGCUU and CCACACC.

16. The method according to claim 13, characterized in that, the first strand of the double-stranded RNA or the sense RNA segment of the shRNA is substantially identical to a target sequence in the Nemo-like kinase gene, the target sequence in the Nemo-like kinase gene comprises a sequence set forth as anyone in SEQ ID NO: 1-39.

17. The method according to claim 13, characterized in that, the lentivirus vector is selected from anyone of the group consisting of pLKO.1-puro, pLKO.1-CMV-tGFP, pLKO.1-puro-CMV-tGFP, pLKO.1-CMV-Neo, pLKO.1-Neo, pLKO.1-Neo-CMV-tGFP, pLKO.1-puro-CMV-TagCFP, pLKO.1-puro-CMV-TagYFP, pLKO.1-puro-CMV-TagRFP, pLKO.1-puro-CMV-TagFP635, pLKO.1-puro-UbC-TurboGFP, pLKO.1-puro-UbC-TagFP635, pLKO-puro-IPTG-1xLacO, pLKO-puro-IPTG-3xLacO, pLP1, pLP2, pLP/VSV-G, pENTR/U6, pLenti6/BLOCK-iT-DEST, pLenti6-GW/U6-laminshrna, pcDNA1.2/V5-GW/lacZ, pLenti6.2/N-Lumio/V5-DEST, pGCSIL-GFP and Lenti6.2/N-Lumio/V5-GW/lacZ.

18. The method according to claim 12, characterized in that, an isolated target oligonucleotide segment of the administering molecule comprises NLK gene segment, except for the oligonucleotide segment of a full-length NLK gene.

19. The method according to claim 18, characterized in that, the oligonucleotide sequence is substantially identical to at least 10, 15, 20, 25, 30, 35, 40, 45, or 50 consecutive nucleotides of the nucleotide sequence of the full-length NLK gene.

20. The method according to claim 18, characterized in that, the oligonucleotide sequence comprises the nucleotide sequence set forth in any one of SEQ ID NO 1-39.

21. A method for preventing or treating tumor in a subject, which method includes: administering an effective amount of a pharmaceutical composition into the subject, wherein the pharmaceutical composition comprises: a molecules which specifically inhibits the transcription or translation of a Nemo-like kinase gene, or specifically inhibits the expression or activity of a Nemo-like kinase protein, and wherein the molecule is a nucleic acid targeted to SEQ ID NOs: 1-39 or wherein the molecule is a shRNA comprising SEQ ID NO:40.

22. The method according to claim 21, characterized in that, the tumor is selected from the group consisting of lung cancer, breast cancer and prostate cancer.

23. The method according to claim 21, characterized in that, the growth, proliferation, recurrence and/or metastasis of the tumor is inhibited.

24. The method according to claim 21, characterized in that the subject is human.

25. The method according to claim 21, characterized in that, the molecule is:
a) a double-stranded RNA comprising a nucleotide sequence that hybridizes under stringent conditions to the Nemo-like kinase gene; or
b) a shRNA comprising a nucleotide sequence that hybridizes under stringent conditions to the Nemo-like kinase gene, or
c) an interference lentivirus vector, which is the lentivirus vector comprising gene segment encoding and expressing the shRNA in b).

* * * * *